United States Patent [19]

Iwakoshi

[11] Patent Number: 4,805,597
[45] Date of Patent: Feb. 21, 1989

[54] ENDOSCOPIC APPARATUS

[75] Inventor: Keiichi Iwakoshi, Nasu, Japan

[73] Assignee: Kabushiki Kaisha Toshiba, Kawasaki, Japan

[21] Appl. No.: 101,641

[22] Filed: Sep. 28, 1987

[30] Foreign Application Priority Data

Sep. 30, 1986 [JP] Japan ................................. 61-229700

[51] Int. Cl.⁴ ............................................... A61B 1/00
[52] U.S. Cl. .......................................................... 128/4
[58] Field of Search ........................................ 128/4, 6

[56] References Cited

U.S. PATENT DOCUMENTS 3,178,994 4/1965 Lang ..................................... 128/6 X
4,704,007 11/1987 Landre et al. ....................... 128/6 X Primary Examiner—William H. Grieb
Attorney, Agent, or Firm—Foley & Lardner, Schwartz, Jeffery, Schwaab, Mack, Blumenthal & Evans

[57] ABSTRACT

An endoscopic apparatus comprises an imaging element disposed at an end of the apparatus, and an operating device for setting the position of a region of interest provided by the imaging element by an operator's one hand, and enlarging and reducing the set region of interest in size by the operator's one hand.

6 Claims, 5 Drawing Sheets

ENDOSCOPIC APPARATUS

The present invention relates to an improvement of an endoscopic apparatus for medical application, and, more particularly, to an electronic endoscopic apparatus in which a region of interest is manually set and enlarged and reduced in size by an operator's one hand at the real time during the operation of the apparatus.

BACKGROUND OF THE INVENTION

An electronic endoscopic apparatus is widely used for medical care and examination of a duodenum, a rectum, a large intestine, an oesophagus, ears, a nose, bladders, etc., of a human organism.

FIG. 1 shows a conventional electronic endoscopic apparatus comprising an end tip portion 3A for housing an optical system such as a solid imaging element which is a charge coupled device (CCD), a curved end portion 3B moved upward, downward, rightward and leftward by the manual operation of an operator, a hand operating portion 1 disposed at the rear end of the endoscopic apparatus, and a connecting portion 2 for optically and electrically connecting these end portions 3A and 3B to the hand operating portion 1.

In the hand operating portion 1, there are disposed a knob for adjusting the angle of the curved end portion 3B, and a plurality of buttons for supplying air and water, and sucking the used air and water to clean a lens disposed in the end tip portion 3A.

Accordingly, an operator normally grips the operating portion 1 by his left hand, and operates the buttons by his index and middle fingers, and performs an orientation for a patient and operates the connecting portion 2 by his right hand.

In the conventional electronic apparatus mentioned above, a region of interest (ROI) is set by CCD and is displayed on a television monitor, and an operator examines and treats a patient while observing the ROI. The set ROI must be changed by a means for changing the ROI disposed on a separate operation table. However, since the operator uses both his right and left hands as mentioned above, it is impossible for the operator to perform the operation for changing the ROI at the real time.

In the fields using X ray, CT scanning, and nuclear medical science, it is well known that the ROI is set on a monitor screen and the set ROI is enlarged or reduced in size and thereafter an image processing is performed in the ROI. However, such operations are performed by a means for setting the ROI such as a joystick, a track ball, a mouse, etc., and such ROI setting means is disposed in an operation table for example and accumulated data are read out later and are displayed on a monitor and the treatment is performed with respect to the displayed image so that the ROI is not set at the real time.

It is often necessary to enlarge a specified portion of the ROI on the monitor screen in the examination and treatment of the patient using an electronic endoscopic apparatus. Such an operation cannot be performed at the real time in the conventional electronic endoscopic apparatus.

SUMMARY OF THE INVENTION

Accordingly, an object of the present invention is to provide an electronic endoscopic apparatus in which a ROI is set and the set ROI is enlarged or reduced in size by one hand operation of an operator at the real time.

With the above object in view, an endoscopic apparatus in the present invention is characterized in that a switch for setting the ROI is disposed in a hand operating portion and can move the ROI upward, downward, rightward and leftward and can enlarge and reduce the set ROI in size.

The switch for setting the ROI comprises a push button for moving the central point of the ROI upward, downward, rightward and leftward, and a two-stage switching push button for enlarging and reducing the ROI in size and cancelling the enlargement and reduction of the ROI. The ROI setting switch is disposed in the hand operating portion in a position in which the operator can operate the switch by his one hand's thumb.

In the endoscopic apparatus in the present invention, since the ROI setting switch is disposed in the hand operating portion and can move the central point of the ROI upward, downward, rightward and leftward, and can enlarge and reduce the set ROI in size, the operator can manually and easily operate the ROI setting switch by his one hand's thumb at the real time so as to set the ROI and enlarge and reduce the set ROI in size, thereby exactly and rapidly examining and treating a patient.

BRIEF DESCRIPTION OF THE DRAWINGS

The present invention will be more apparent from the following description of the preferred embodiments thereof in conjunction with the accompanying drawings in which.

DETAILED DESCRIPTION OF THE PREFERRED EMBODIMENTS

The preferred embodiments of an endoscopic apparatus in the present invention will now be described in detail with reference to the drawings.

Figure 1:
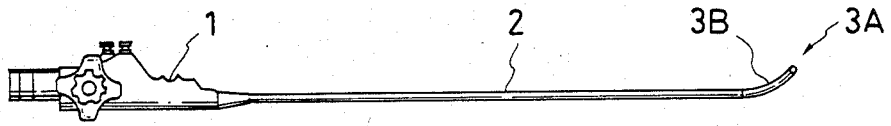
FIG. 1 is a perspective view showing a conventional electronic endoscopic apparatus.
Figure 2:
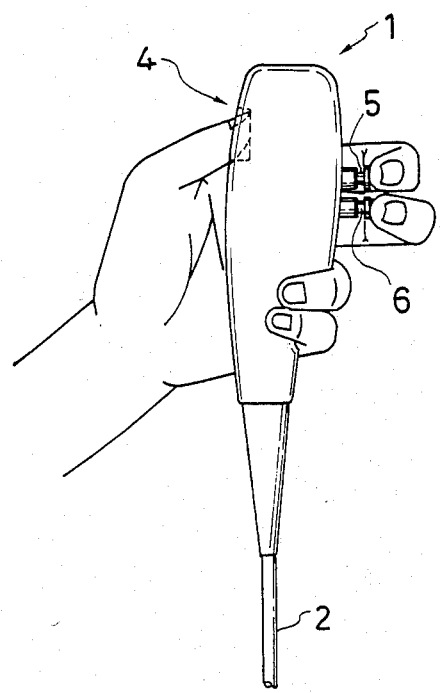
FIG. 2 is a perspective view showing a state in which an operator grips a hand operating portion of an electronic endoscopic apparatus in the present invention.

As shown in FIG. 2, an endoscopic apparatus in the present invention comprises a button 5 for supplying air and water to an objective lens to clean the objective lens, a button 6 for sucking the used air and water from the objective lens, and a switch 4 for setting a region of interest (ROI). The ROI setting switch 4 and the buttons 5 and 6 are disposed in a hand operating portion 1 connected to a connecting portion 2 at the rear end thereof. While an operator holds the hand operating portion 1 by his left hand for example, the operator can operate the ROI setting switch 4 by his left hand's thumb and can operate the buttons 5 and 6 by his left hand's index and middle fingers, etc.

Figure 3:
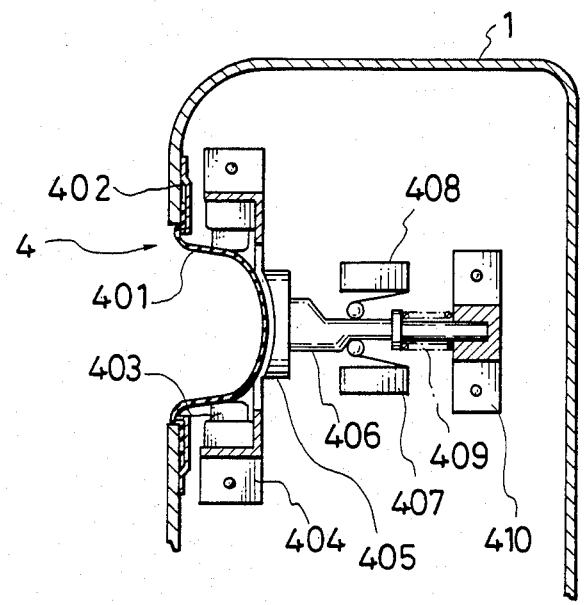
FIG. 3 is a sectional view showing one embodiment of a ROI setting switch in the electronic endoscopic apparatus of the present invention.

The ROI setting switch 4 has a recessed portion for receiving one hand's thumb of the operator as shown in FIG. 3. Namely, the ROI setting switch 4 comprises four push buttons 403 (two such buttons are shown in FIG. 3) for moving the central point of the ROI upward, downward, rightward and leftward, and a two-stage switching push button 405 disposed in the central portion of the push buttons 403 and enlarging and reducing the ROI in size. The push buttons 403 and 405 are covered by a switch cover 401 made of rubber for example and are disposed within the main body of the hand operating portion 1.

In FIG. 3, reference numerals 402 and 404 are respectively a cover attaching plate and a switch attaching plate.

The two-stage switching push button 405 is connected to two microswitches 407 and 408 through a shaft 406. When the switching push button 405 is manually and weakly pushed by one step, the switch 407 is turned on, and when the switching push button 405 is thereafter strongly pushed, the switch 408 is turned on. This switching operation is performed through the shaft 406, a spring 409 disposed around the shaft 406, and a guide member 410 receiving the shaft 406 and contacting the spring 409.

Figure 4:
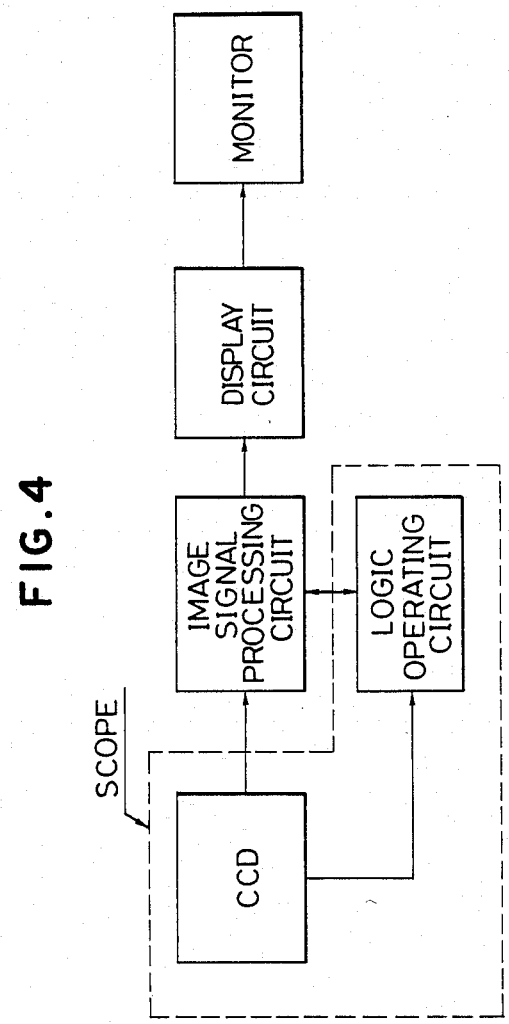
FIGS. 4 and 5 are schematic views showing electronic circuits in the electronic endoscopic apparatus of the present invention.
Figure 5:
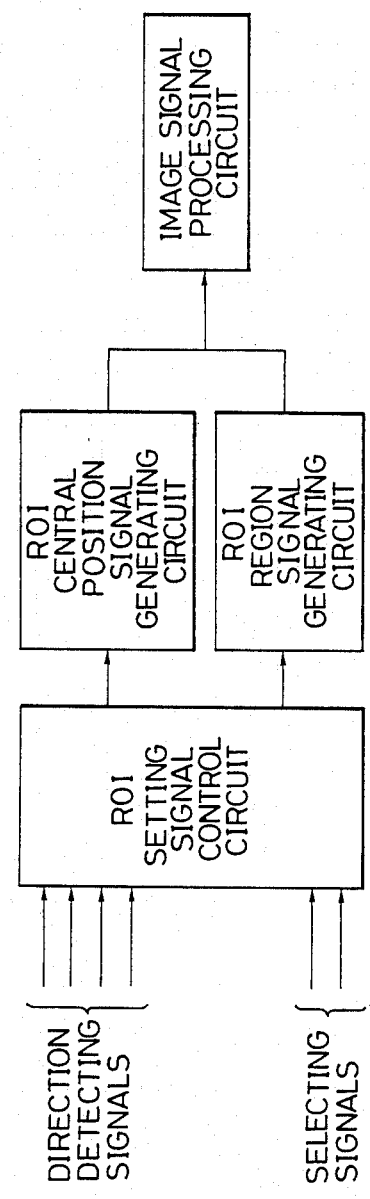

The electronic endoscopic apparatus constituted above comprises an electronic circuit including a main portion thereof as shown in FIG. 4 and a logic operating circuit therefor as shown in FIG. 5.

Namely, directional signals are output from the four buttons 403 with respect to the upward, downward, rightward and leftward directions of the central point of the ROI, and selecting signals are output from the central button 405, thereby setting the position of the ROI and setting the ROI.

The operation of the electronic endoscopic apparatus of the present invention having the above constitution and circuit will be now described.

When an operator finds a diseased portion of a patient for example and the switching button 405 is then pushed to turn on the switch 407, the setting of a ROI is started, and when the four push buttons 403 are then selectively pushed, the central point of the ROI is moved to a predetermined place and is displayed on a monitor screen.

When the central point of the ROI has been set in the predetermined place, the central push button 405 is weakly pushed again so that the switch 407 is turned on again, thereby setting the minimum ROI.

Next, the ROI is gradually enlarged in size as the central push button 405 is pushed stepwise. When a predetermined enlarged ROI has been displayed on the screen, the central push button 405 is strongly pushed so that the switch 408 is turned on, thereby completing the setting of the enlarged ROI on the screen.

When the central button 405 has been strongly pushed and this state is held for more than one second, the enlargement of the ROI is cancelled and the original minimum ROI is again displayed on the screen.

As mentioned above, the central push button 405 is constituted such that the minimum ROI is set on the screen and the ROI is enlarged and the enlarged ROI is set by strongly pushing the central push button and is cancelled, constituting a two-stage switching type. Accordingly, it is possible to manually start the setting of the ROI, the setting of the central point of the ROI, the enlargement of the ROI and the cancelling thereof.

In summary, the operator can operate the ROI setting switch 4 by his one hand to easily set the ROI and enlarge the ROI and cancel the enlargement of the ROI at the real time.

In the embodiment mentioned above, the ROI setting switch 4 has a recessed portion in the hand operating portion 1, but may have a projected portion instead of the recessed portion in the hand operating portion.

Figure 6:
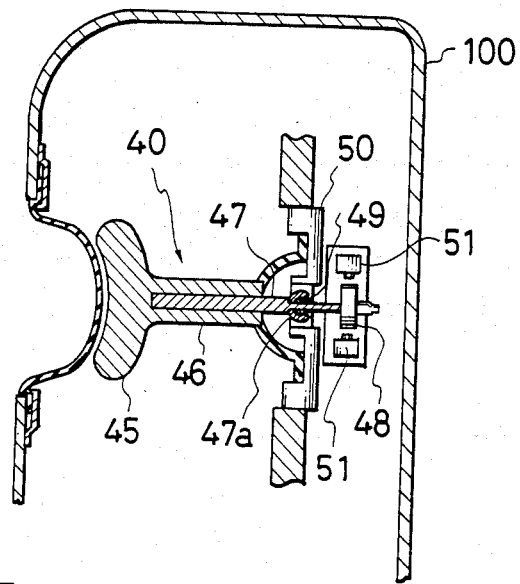
FIGS. 6 and 7 are sectional views showing another embodiment of the ROI setting switch.

FIG. 6 shows another embodiment of the endoscopic apparatus in the present invention. In FIG. 6, a switch device 40 for setting a ROI disposed within a hand operating portion 100 comprises a recessed second operating portion 45, a shaft portion 46 connected to the second operating portion 45, an extension 47 extending from the shaft portion 46 and having a recessed portion 47a, and a contacting portion 48 connected to an end of the extension 47. The recessed portion 47a of the extension 47 is pivotally supported by a support portion 49 which is generally spherical for example and is attached to a support member 50. The contact portion 48 is located between a pair of up and down switches 51, and is separated from the pair of switches 51 when the contact portion 48 takes a neutral position. The contact portion 48 is also located between unillustrated right and left switches, and is separated from the right and left switches when the contact portion 48 takes a neutral position.

In the endoscopic apparatus mentioned above, when an operator moves the second operating portion 45 in the upward or downward direction in FIG. 6, the contacting portion 48 moved together with the second operating portion 45 is pivoted around the support portion 49 in the downward or upward direction so that the contacting portion 48 contacts and actuates the down or up switch 51, respectively. Further, when the second operating portion 45 is moved in the right or left direction, the contacting portion 48 is pivoted around the support portion 49 in the left or right direction so that the contacting portion 48 contacts and actuates the left or right switch, respectively. Accordingly, in the switch device 40 for setting the ROI as constituted in FIG. 6, it is not necessary to separately operate the four push buttons 403 as in FIG. 3, and the central point of the ROI can be moved upward, downward, rightward and leftward by operating the single second operating portion 45.

Figure 7:
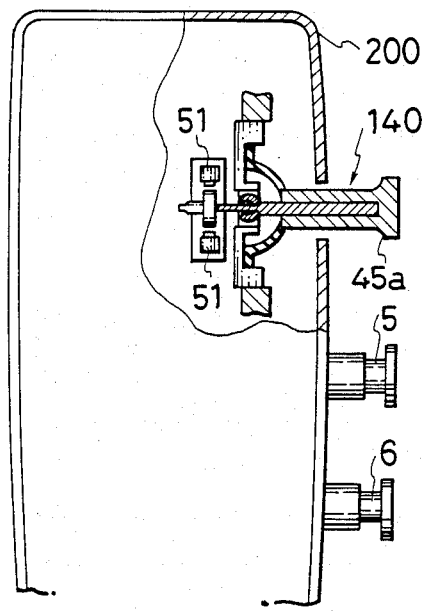

In FIG. 6, the switch device 40 for setting the ROI is disposed to be opposite the button 5 for supplying air and water and the button 6 for sucking the used air and water. However, as shown in FIG. 7, a switch device 140 similar to the ROI setting switch device 40 and disposed in a hand operating portion 200 may be disposed on the same side as the side of the air and water supplying button 5 and the sucking button 6. In FIG. 7, the head of a second operating portion 45a is different in shape from the head of the second operating portion 45 of FIG. 6, and has a shape similar to the shape of the heads of the buttons 5 and 6. It will be understood that the effects of the present invention can be obtained even in the endoscopic apparatus shown in FIGS. 6 and 7.

As mentioned above, in an endoscopic apparatus in the present invention, an end tip portion thereof, which constitutes a charge coupled device, is moved upward, downward, rightward and leftward to set a ROI, and the set ROI is enlarged and reduced in size and the enlarged ROI is cancelled, using a ROI setting switch disposed in a position in which the switch can be operated by an operator's one hand thumb in a hand operating portion. Accordingly, the operator can easily set the ROI and enlarge and reduce the set ROI and cancel the enlarged ROI so that the examination and the treatment of a patient can be exactly and rapidly performed.

What is claimed is:

1. An endoscopic apparatus comprising:
an imaging element disposed at an end of the apparatus; and
operating means for setting the position of a region of interest provided by the imaging element by an operator's one hand, and enlarging and reducing the set region of interest in size by the operator's one hand,
wherein said operating means comprises a switch for moving the region of interest upward, downward, rightward and leftward to set the position of the region of interest, and for enlarging and reducing the set region of interest.

2. An endoscopic apparatus as claimed in claim 1, wherein said switch comprises a push button for moving the central point of the region of interest upward, downward, rightward and leftward, and a two-stage switching push button for enlarging and reducing the set region of interest.

3. An endoscopic apparatus as claimed in claim 1, wherein said switch is disposed in a hand operating portion in a position in which the switch can be operated by the thumb of the operator's one hand.

4. An endoscopic apparatus as claimed in claim 3, wherein said switch is disposed on one side of the hand operating portion, and an operating button for cleaning the imaging element is disposed on the side opposite the switch.

5. An endoscopic apparatus as claimed in claim 3, wherein said switch and an operating button for cleaning the imaging element are disposed on one side of the hand operating portion.

6. An endoscopic apparatus as claimed in claim 1, wherein said operating means sets the position of the region of interest, and enlarges and reduces the set region of interest at the real time.

* * * * *